United States Patent
Schwab

(10) Patent No.: US 10,208,808 B2
(45) Date of Patent: Feb. 19, 2019

(54) RELEASABLE COUPLING AND ENDOSCOPIC INSTRUMENT WITH A RELEASABLE COUPLING

(71) Applicant: Richard Wolf GmbH, Knittlingen (DE)

(72) Inventor: Daniel Schwab, Bretten (DE)

(73) Assignee: Richard Wolf GmbH, Knittlingen (DE)

( * ) Notice: Subject to any disclaimer, the term of this patent is extended or adjusted under 35 U.S.C. 154(b) by 239 days.

(21) Appl. No.: 15/079,716

(22) Filed: Mar. 24, 2016

(65) Prior Publication Data

US 2016/0281795 A1  Sep. 29, 2016

(30) Foreign Application Priority Data

Mar. 27, 2015  (DE) .................. 10 2015 205 601

(51) Int. Cl.
*F16D 11/14* (2006.01)
*F16D 27/01* (2006.01)
*A61B 1/00* (2006.01)
*F16D 11/00* (2006.01)

(52) U.S. Cl.
CPC ............ *F16D 11/14* (2013.01); *A61B 1/0016* (2013.01); *A61B 1/00133* (2013.01); *A61B 1/00158* (2013.01); *F16D 27/01* (2013.01); *F16D 2011/008* (2013.01)

(58) Field of Classification Search
CPC ... F16D 1/10–1/12; F16D 11/00–11/16; F16D 23/02; F16D 27/01; A61B 1/00133; A61B 1/0016
See application file for complete search history.

(56) References Cited

U.S. PATENT DOCUMENTS

| | | | | |
|---|---|---|---|---|
| 3,666,064 A | * | 5/1972 | Bird | F16D 23/02 |
| | | | | 192/103 C |
| 3,726,373 A | * | 4/1973 | Miller | F16D 41/22 |
| | | | | 192/35 |
| 5,475,485 A | | 12/1995 | Diener | |
| 5,803,680 A | | 9/1998 | Diener | |
| 2009/0023988 A1 | * | 1/2009 | Korner | A61B 17/1624 |
| | | | | 600/106 |

FOREIGN PATENT DOCUMENTS

| | | | |
|---|---|---|---|
| DE | 10 62 962 B | 8/1959 | |
| DE | 42 41 767 C1 | 12/1993 | |
| DE | 195 37 812 C1 | 1/1997 | |
| GB | 691 413 A | 5/1953 | |
| GB | 851828 A * | 10/1960 | ............ F16D 3/00 |
| JP | 2009 115 236 A | 5/2009 | |

* cited by examiner

*Primary Examiner* — Richard M Lorence
(74) *Attorney, Agent, or Firm* — McGlew and Tuttle, P.C.

(57) ABSTRACT

A releasable coupling for the transmission of a rotation movement. This coupling includes a first and a second coupling half which include engagement structures which correspond to one another and which can positively engage with one another. At least one permanent magnet is arranged on at least one coupling half in a manner such that with the approach of the coupling halves to one another, these with respect to a rotation axis are rotated into a defined angular position relative to one another, by way of the magnetic force which is produced by the permanent magnet.

19 Claims, 11 Drawing Sheets

RELEASABLE COUPLING AND ENDOSCOPIC INSTRUMENT WITH A RELEASABLE COUPLING

CROSS REFERENCE TO RELATED APPLICATIONS

This application claims the benefit of priority under 35 U.S.C. § 119 of German Patent Application 10 2015 205 601.5 filed Mar. 27, 2015, the entire contents of which are incorporated herein by reference.

FIELD OF THE INVENTION

The invention relates to a releasable coupling for the transmission of a rotation movement and to an endoscopic instrument with such a coupling.

BACKGROUND OF THE INVENTION

Endoscopic instruments with which a material removal can be carried out in a difficultly accessible cavity are known in the medical as well as in the technical field. With regard to these instruments, in the context of the invention, it can be the case of endoscopes as well as auxiliary instruments which are applied in combination with endoscopes.

Endoscopes of this type which are also called technoscopes or boroscopes, and which are predominantly provided for repair work on turbine blades in turbine engines are described for example in DE 42 41 767 C1 and DE 195 37 812 C1. These endoscopes in each case compromise an elongate hollow shank with observation optics which are arranged therein and which are optically connected to an eyepiece or camera connection, wherein this eyepiece or camera is arranged at the proximal side of the hollow shank. A tool which is designed for the removal of material is arranged at the distal end of the hollow shank. The material removal is effected by way of a rotation of the tool about its middle axis. This rotation is produced by way of an electric motor which is arranged on a housing connecting proximally to the hollow shank. The movement transmission from the motor shaft of the motor to the tool is effected via a belt drive, wherein the motor shaft is connected via a positive-fit coupling to a drive disc of the belt drive.

The endoscopes which are known from DE 42 41 767 C1 and DE 195 37 812 C1 have proven their worth on application, but it has be found that the assembly of the motor on the endoscope and hereby in particular the creation of the positive connection of a coupling half on the motor shaft side to a coupling half formed by the drive disc of the belt drive is comparatively cumbersome and demands significant manual skill on the part of the user.

SUMMARY OF THE INVENTION

Against this background, it is the object of the invention, to provide a releasable coupling for transmission of a rotation movement, with which a drive-side coupling half can be connected to an output side or a driven-side coupling half in a simple manner. A further object of the invention lies in creating an endoscopic instrument, with which a motor for the drive of a tool which is arranged at the distal end of the instrument can be attached on the instrument in a simpler and quicker manner compared to the known instruments.

The first-mentioned object is achieved by a releasable coupling with the features of the present invention, wherein advantageous further developments of this coupling are to be deduced from the subsequent description as well as the drawings. The solution of the second-mentioned object lies in an endoscopic instrument with the features of the present invention.

The releasable coupling according to the invention serves for transmitting a rotation movement. It comprises two coupling halves which can be joined to one another whilst forming a positive fit. The joining-together of the coupling halves is effected by way of a movement of the coupling halves to one another in the direction of the rotation axis of the coupling. The coupling halves can be separated from one another again and the coupling can therefore be released, by way of an opposite movement.

The two coupling halves comprise engagement means which correspond to one another and which on joining together the coupling halves can positively engage with one another, for forming the positive fit with one another. This engagement is only possible if the engagement means of the two coupling halves have an angular position which corresponds to one another. According to the invention, at least one permanent magnet is arranged on at least one coupling half in a manner such that when the coupling halves approach one another, these are rotated into a defined angular position relative to one another with respect to the rotation axis of the coupling, by way of the magnetic force which is produced by the permanent magnet, in order to create this angular position of the engagement means which is necessary for the mutual engagement, without having to accordingly manually align one of the two coupling halves for this, wherein the engagement means which are provided on the two coupling halves lie directly opposite one another in the defined angular position of the two coupling halves, preferably in the direction of the rotation axis of the coupling, and can engage with one another with a further approach of the coupling halves in the direction of the rotation axis of the coupling. The magnetic force which is produced by the at least one permanent magnet preferably serves for the alignment of the coupling halves to one another, but not for the force transmission in the coupled condition. The force or torque transmission is effected via the positive engagement of the engagement means.

A magnetic attraction force as well as a magnetic repulsion force can be utilized for producing the rotation movement of the two coupling halves relative to one another. With the use of a magnetic attraction force, for example a design with which in each case at least one permanent magnet and preferably in each case several permanent magnets are provided on both coupling parts and which are arranged on the coupling halves in a manner in which they interact with one another in an attracting manner is conceivable. In this case, the permanent magnets of the two coupling halves seek to move into a position, in which the field strength of the magnetic field existing between the permanent magnets of the two coupling halves, which is to say the attraction force between the permanent magnets is greatest. The arrangement of the permanent magnets on the coupling halves is hereby usefully such that the magnetic field strength is then at its greatest when the engagement means arranged on the coupling halves are located in such a position, in which they can engage into one another. Merely at least a section of a magnetizable material can be provided on one of the coupling halves instead of the at least one permanent magnet which is arranged there, wherein this material interacts in an attracting manner with the at least one permanent magnet arranged on the other coupling halve, as an alternative to the use of permanent magnets which are arranged on both coupling halves and which interact with one another in an attracting manner.

According to the invention however, a design of the coupling, with which a magnetic repulsion force is utilized for producing the rotation movement of the coupling halves which is necessary for the alignment of the coupling halves, is preferred. In this context, in a preferred further development of the invention, in each case at least one permanent magnet is arranged on both coupling halves, which is to say on a first and on a second coupling half, wherein the permanent magnets with regard to their poling are aligned in a manner such that they repel one another in the rotation direction of the coupling halves. Hereby, the permanent magnets of the first and second coupling half, amid a relative rotation of the first coupling half with respect to the second coupling half, move away from one another to such an extent, until the magnetic interaction between the permanent magnets of the two coupling halves is so low, that this is no longer sufficient for a further rotation movement of the two coupling halves relative to one another, and the coupling halves come to a standstill. The permanent magnets are hereby usefully arranged on the two coupling halves such that the engagement means which are arranged on the two coupling halves are then located in such a position, in which they can engage into one another when the magnetic interaction between the at least one permanent magnet arranged on the first coupling half and the at least one permanent magnet arranged on the second coupling half causes no further rotation movement of the two coupling halves relative to one another.

The permanent magnets are preferably aligned in the direction of the rotation axis of the coupling, wherein the permanent magnets of the coupling halves which lie opposite one another face one another with the same pole. The permanent magnets can therefore be aligned in each case on the first coupling half such that their north poles face the second coupling half in the connection direction of the two coupling halves, wherein the permanent magnets which are arranged on the second coupling half are aligned in a manner such that their north poles point to the first coupling half in the connection direction of the two coupling halves. As an alternative to this, there is also the possibility of arranging the permanent magnets of the two coupling halves in such an aligned manner that in each case the south poles of the permanent magnets of one coupling half face the respective other coupling half. The permanent magnets of the first coupling half repel the permanent magnets of the second coupling halve since the permanent magnets of the two coupling halves face the respective opposite coupling half with the same pole. The repulsion forces between the permanent magnets of the first and second coupling halves hereby although acting predominantly in the direction of the rotation axis of the coupling which is to say in the direction, in which the coupling halves are moved to one another for creating the coupling, however the repulsion fields at the poles of the permanent magnets and which act between the permanent magnets of the first and second coupling half also extend to a certain extent transversely to the direction of the rotation axis of the coupling in the rotation direction of the coupling, so that the permanent magnets of the first coupling half are moved away from the permanent magnets of the second coupling half amid a relative rotation of the first coupling half with respect to the second coupling half, on account of the repulsion forces which result from this.

The permanent magnets are further preferably arranged on the front sides of both coupling halves which in each case face the other coupling half. Hereby, the front sides of the two coupling halves is to be understood as the sides of these coupling halves which are arranged closest to the respective other coupling half with the approach of the coupling halves. The permanent magnets of the two coupling halves, with the approach of the coupling halves to one another, can be arranged very closely to the permanent magnets of the respective other coupling half, by way of the permanent magnets being arranged on these front sides, and this ensures a comparatively large magnetic interaction between the at least one permanent magnet of the first coupling half and the at least one permanent magnet of the second coupling half, by which means an adequately large torque is provided for the rotation of the coupling halves to relative to one another.

According to a further advantageous design of the coupling according to the invention, in each case at least one projection which engages into a recess which is formed in each case on the other coupling half is formed on the first and the second coupling half. Accordingly, the projections and the recesses which correspond to these, on the two coupling halves form the engagement means which effect the positive connection of the two coupling halves to one another. Usefully, a permanent magnet is integrated in each case in the projection or in the projections, which are formed on the two coupling halves. Hereby, it is necessary for the permanent magnets of the two coupling halves to be aligned such that they face the respective opposite coupling half with the same pole, since the permanent magnets in the joined-together condition of the two coupling halves are arranged offset relative to one another with respect to the periphery of the coupling halves.

Usefully, the two coupling halves are formed from a non-magnetizable material. This measures serves for producing clearly defined magnetic fields which is to say ones which are spatially delimited, between the coupling halves. Basically, all non-ferro-magnetic materials can be used as a material for the two coupling halves, wherein on selecting the material one however is to take into account the fact that the intrinsic stiffness of the materials must permit the transmission of a required torque from the one to the other coupling half.

Preferably, each of the coupling halves comprises several permanent magnets which are arranged in a manner uniformly distributed over their periphery, wherein usefully equal numbers of permanent magnets are present on both coupling halves. Accordingly, in each case several permanent magnets are arranged successively in the peripheral direction of the respective coupling half, on the first as well as on the second coupling half, wherein all permanent magnets have the same distance to the permanent magnets which are arranged directly adjacent to them. The use of several permanent magnets which are arranged on the coupling halves in the described manner, to a particular extent serves for ensuring that the coupling halves align themselves in the desired manner as a result of the magnetic forces exerted by the permanent magnets, independently of the angular offset existing between the coupling halves, when joining together the coupling which means when the coupling halves approach one another.

Further preferably, the permanent magnets on the coupling halves are in each case arranged at the same radial distance to a rotation axis of the coupling halves. The arrangement of the permanent magnets on the two coupling halves is accordingly such that given an angular offset existing between the coupling halves, they completely or at least partly overlap when they approach one another in the direction of the rotation axis of the coupling halves. This measure is also directed towards effecting an as large as possible magnetic interaction between the permanent magnets of the first and the second coupling halves.

Advantageously, the permanent magnets which are arranged on the first and the second coupling halves are each arranged at the greatest possible radial distance to the rotation axis of the coupling. Accordingly, the permanent magnets on the two coupling halves are preferably arranged in the direct vicinity to the outer periphery of the respective coupling half. The advantage of this design lies in the fact that the magnetic forces which are produced on account of the magnetic interaction between the permanent magnets arranged on the first coupling half and the second coupling half, transversely to the rotation axis of the coupling halves, effect an as large as possible torque.

The releasable coupling according to the invention is preferably designed as a jaw coupling which is simple with regard to design, wherein a permanent magnet is integrated in each case in each jaw of the two coupling halves. This means that at least one projection which projects in the connection direction of the two coupling halves and is designed as a jaw is formed on both coupling halves, in which projection a permanent magnet is integrated and which engages into a recess formed on the other coupling half, on joining together the two coupling halves. Preferably several projections which are distanced to one another in the peripheral direction of the coupling halves, are formed on the two coupling halves in a manner distributed over their periphery, wherein the projections of the first coupling half engage into the intermediate spaces between the projections of the second coupling half. Hereby, the peripheral dimensions of the projections of one coupling half correspond to the peripheral dimensions of the intermediate spaces between the projections of the respective other coupling half, for forming a positive fit between the first and the second coupling half.

With a coupling designed as a jaw (claw) coupling, it has further been found to be advantageous if the ends of the permanent magnets are aligned in each case to a face side of the jaws. The permanent magnets are thus preferably integrated in the jaws of the jaw coupling such that an end of the permanent magnets terminates in a flush manner with a face side of the jaws which faces the respective other coupling half. This design permits the permanent magnets of the two coupling halves to be brought as closely as possible to one another with the approach of the coupling halves, wherein the permanent magnets are protected from damage due to their complete arrangement within the jaws.

The endoscopic instrument according to the invention is predominantly envisaged for the technical application, which is to say for machining or post-machining a technical component in difficultly accessible cavities, but it can also be the case of an instrument which is applied in the medical field, and which in body cavities of living beings permits a manipulation of organ and tissue structures and preferably also permits a removal of tissue there. A movable tool is arranged on the distal end of the instrument for this purpose and for the removal of material on technical components. This tool can be an instrument which rotates about its middle axis, as well as a tool which is movable in an oscillating manner in the longitudinal direction of the endoscopic instrument, wherein the tool can be arranged on the distal end of the instrument in a stationary manner or in a manner bendable transversely to the longitudinal extension of the instrument.

The tool is actively connected to a motor via a coupling, for producing the movement of the tool. With regard to the coupling, it is the case of a coupling with the previously described features, wherein a first coupling half is preferably coupled in movement to the tool via a gear, and a second coupling half is connected to the motor shaft of the motor which is preferably designed as an electric motor. The motor can be attached on the instrument in a quick and simple manner by way of the use of this coupling, since an angular offset which exists with respect to the engagement means provided on both coupling halves is automatically eliminated by the coupling by the magnetic force of the at least one permanent magnet which is provided on the coupling, by way of the coupling halves rotating relative to one another into a defined angular position.

The present invention is described in detail below with reference to the attached figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
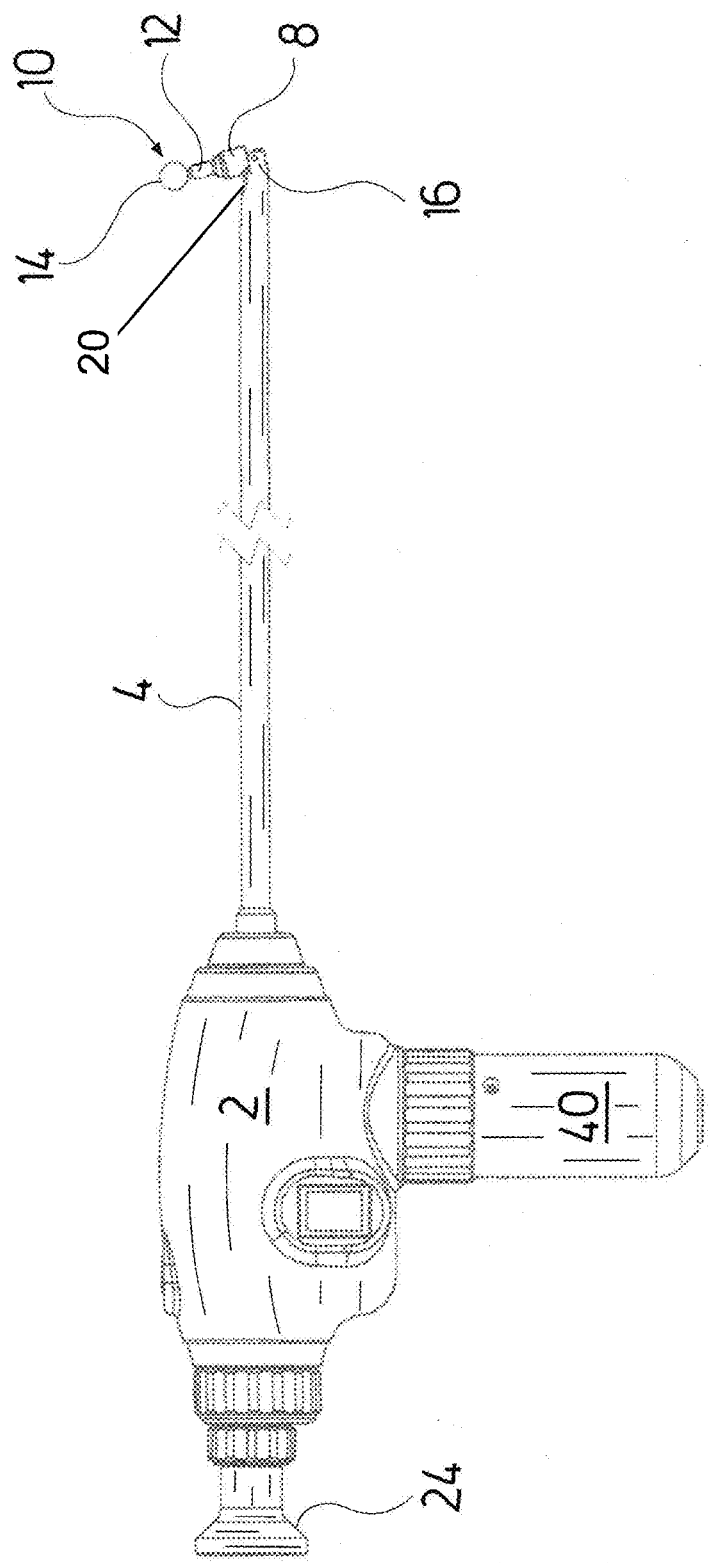
FIG. 1 is a lateral view of an endoscopic instrument.
Figure 2:
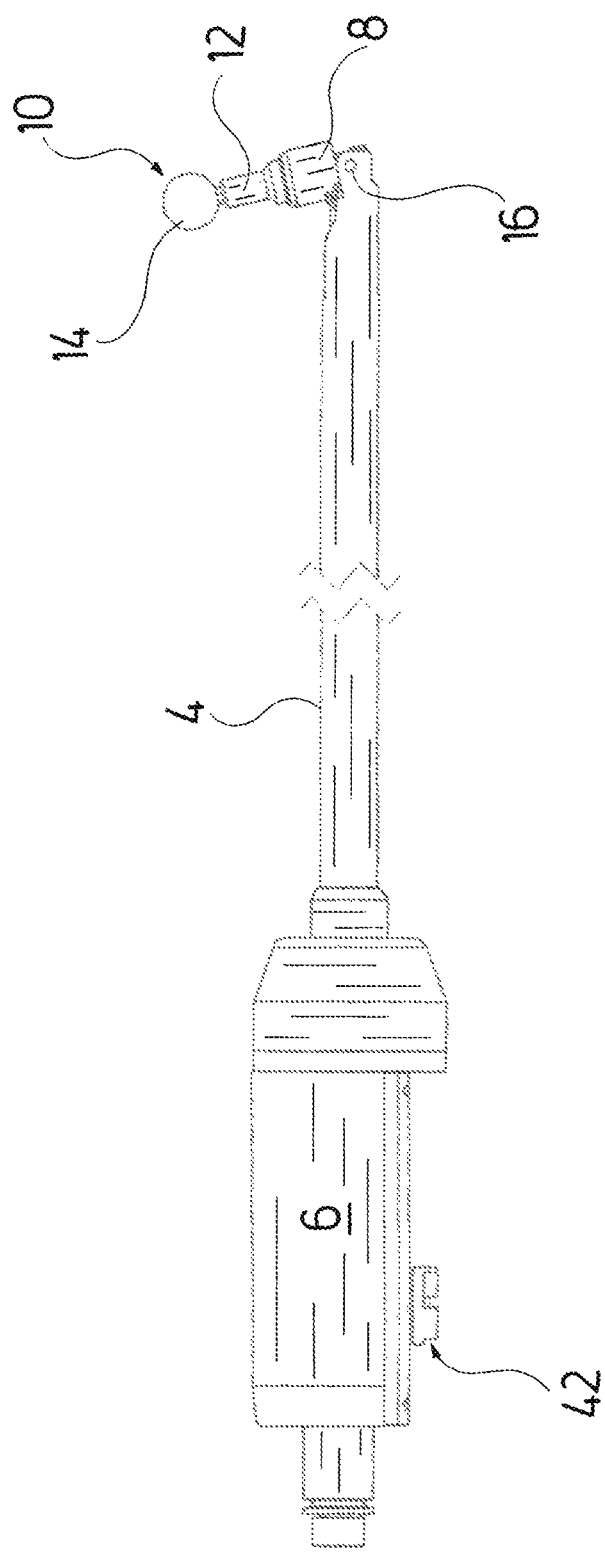
FIG. 2 is a view of the endoscopic instrument according to FIG. 1 whilst omitting a proximal housing and a housing attachment connecting on the housing.
Figure 3:
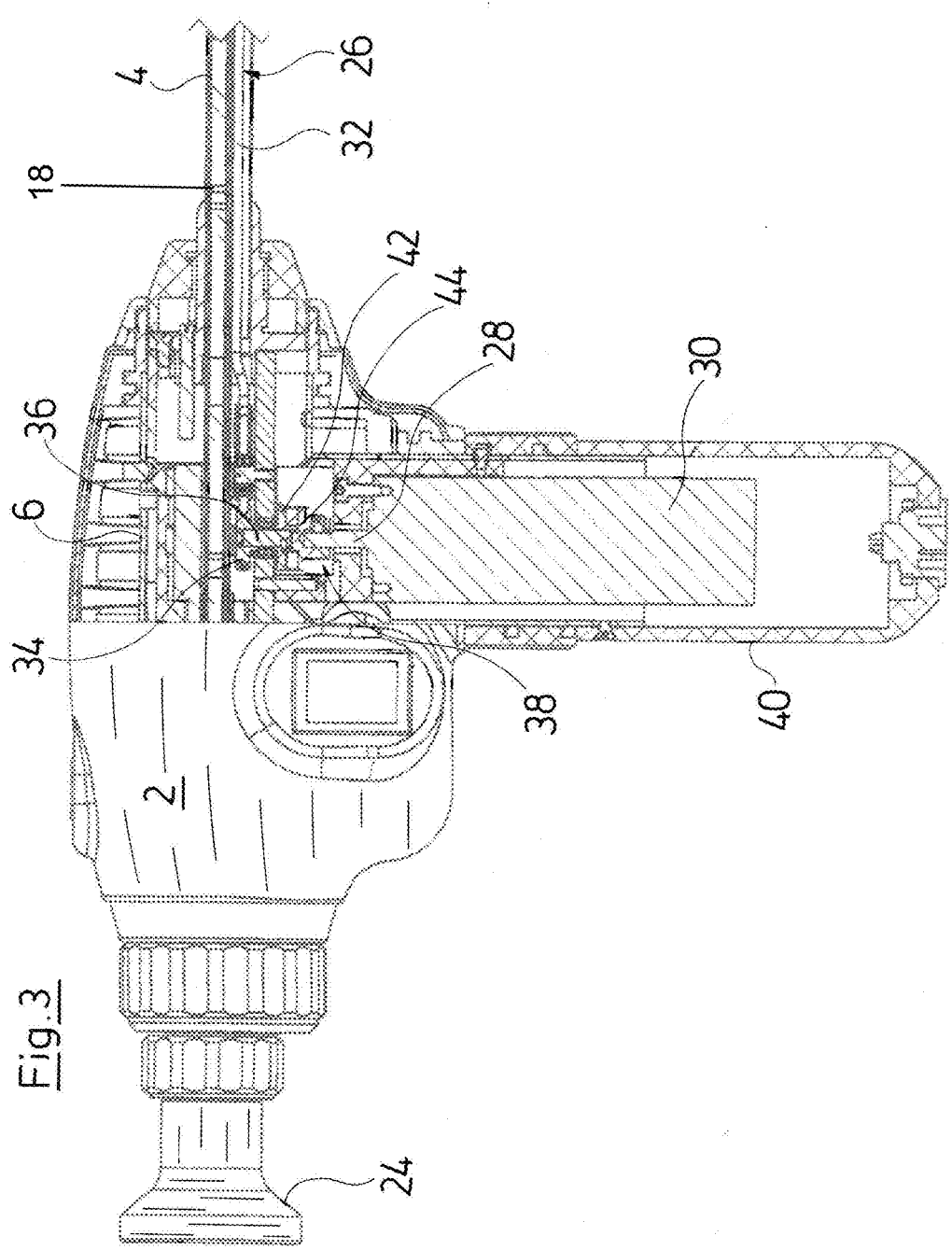
FIG. 3 is a partial sectional view of a proximal end region of the endoscopic instrument according to FIG. 1 in a first representation.
Figure 4:
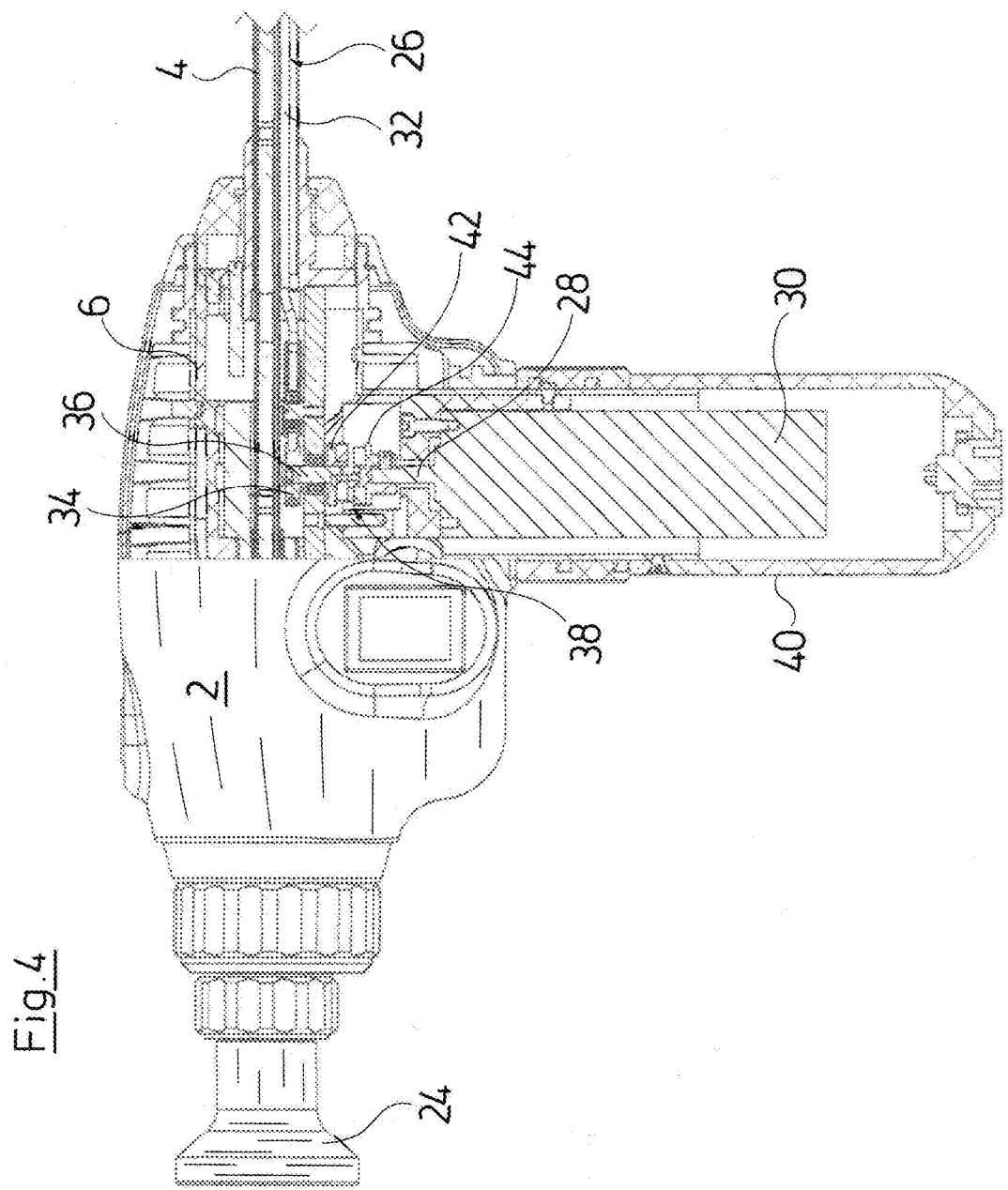
FIG. 4 is a partial sectional view of a proximal end region of the endoscopic instrument according to FIG. 1 in a second representation.
Figure 5:
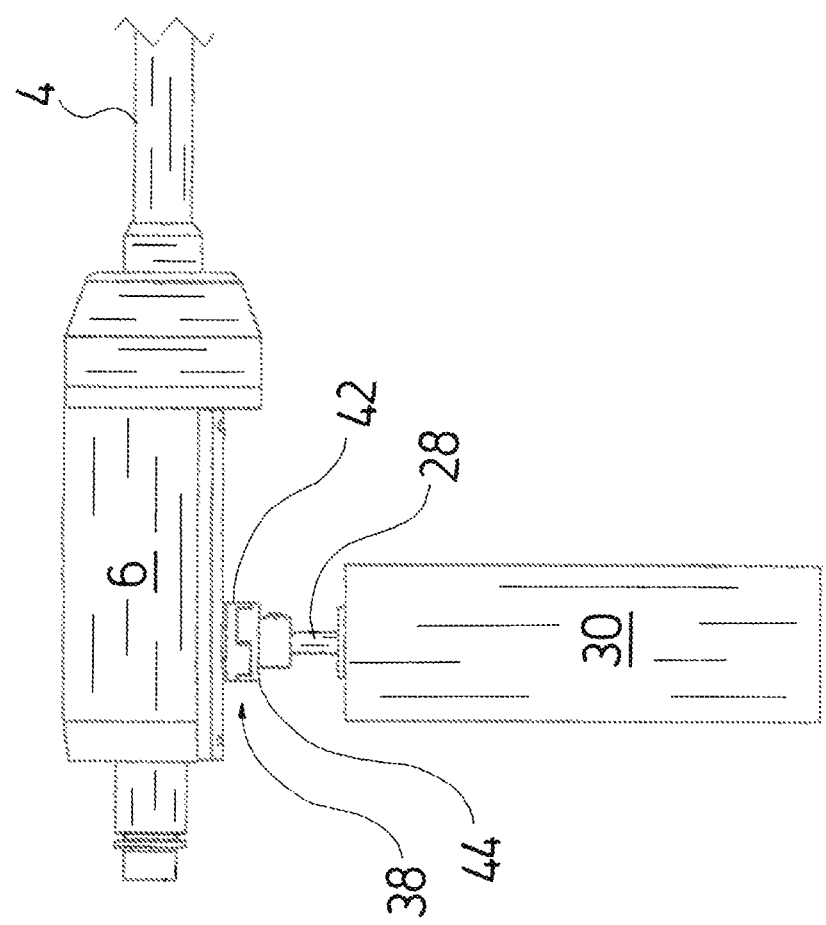
FIG. 5 is a view of the representation according to FIG. 2 with a motor which is connected via a coupling to the endoscopic instrument.
Figure 6:
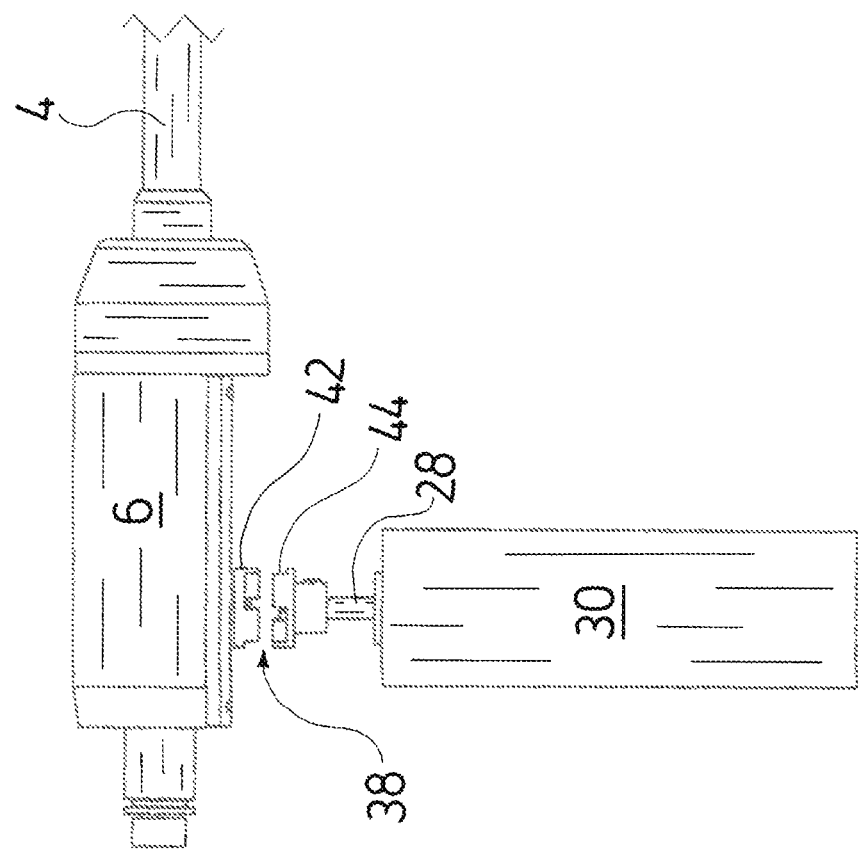
FIG. 6 is a view of the representation according to FIG. 5, with the coupling in the non-coupled condition (state)

The endoscopic instrument which is represented in the drawings comprises a housing 2, at the distal side of which a tubular hollow shank 4 is arranged. The hollow shank 4 is designed in a straight and rigid, longitudinally extended manner and at the proximal side is connected to an inner housing 6 which is arranged in the longitudinal extension of the hollow shaft 4 and is arranged in the housing 2.

A receiver 8 for a tool 10 is arranged at the distal end of the hollow shank 4. The tool 10 comprises a shank 12, at whose distal end a spherical machining head 14 is arranged for removing material. The tool 10 by way of the shank 12 is rotatably mounted in the receiver 8 about a rotation axis which is formed by the shank 12.

The receiver 8 is fastened on the hollow shank 4 by way of bearing pins 16, wherein the bearing pins 16 form an axis, about which the receiver 8 with the tool 10 mounted therein can be bent from an initial position, in which the receiver 8 with the tool is arranged in the direct longitudinal extension of the hollow shank 4, into a direction transverse to the longitudinal extension of the hollow shank 4. The receiver 8 is coupled in movement to a push-pull element guided through the hollow shank 4 to the housing 2, for the control of the bending of the receiver 8 with the tool 10 which is mounted therein. This push-pull element and also the other components for the control of the bending of the receiver 8 are generally known from the state of the art, for example from DE 42 41 767 C1 and corresponding U.S. Pat. No. 4,475,485 A, the entire contents of which are incorporated herein by reference, and are not represented in the drawings for the purpose of a better overview.

A window 18 is formed on the distal end of the hollow shank 4, on a peripheral region of the hollow shank 4 which is directed in the direction of the bending of the receiver 8. A channel 20, into which an endoscope is introduced, extends through the hollow shank 4 and the inner housing 6, departing from this window 18, wherein the eyepiece 24 of the endoscope projects out of the instrument at the proximal end of this.

The shank 12 of the tool is actively connected to a motor shaft 28 of a motor 30 via a belt drive 26, for producing the rotation movement of the tool 10. With regard to the motor 30 it is the case of an electric motor. The belt drive 26 corresponds essentially to a belt drive which is known from DE 42 41 767 C1 and corresponding U.S. Pat. No. 4,475,485 A, with an endless belt 32 which wraps a belt disc which is arranged at the distal end of the hollow shank 4 and which is not represented in the drawings for the purpose of a better overview, and a belt pulley 34 which is arranged in the inner housing 6 arranged at the proximal side of the hollow shank 4.

The belt pulley 34 is connected in a rotationally fixed manner to a drive shaft 36 mounted in a rotatable manner about its middle axis in the inner housing 6. The drive shaft 36 is aligned normally to the longitudinal extension of the hollow shank 4, wherein the end of the drive shaft 36 which is away from the belt pulley 34 projects out of the inner housing 6. The drive shaft 36 at this end is releasably connected to the motor shaft 28 of the motor 30 via a coupling 38. The motor 30 is arranged in a housing attachment 40 extending transversely to the longitudinal extension of the housing 2.

The coupling 38 which is designed as a jaw coupling comprises a first coupling half 42 which is connected in a rotationally fixed manner to the drive shaft 36, and a second coupling half 44 which is connected in a rotationally fixed manner to the motor shaft 28. As is particularly evident from FIGS. 7-11, the coupling halves 42 and 44 in each case comprise a circular-disc-like main body 46, from which three projections or jaws 48 extend in the direction of the respective other of the coupling halves 42 and 44. The three jaws 48 of each of the two coupling halves 42 and 44 are arranged adjacent to the outer periphery of the main body 46 and are uniformly distributed over the periphery of the main body 46, wherein intermediate spaces 50 which are thus formed between adjacent jaws 48 serve for receiving the jaws 48 of the respective other coupling half 42 and 44 respectively, in the coupled condition of the coupling 38, and in this manner create a positive connection between the coupling halves 42 and 44. For this purpose, the dimensions of the intermediate spaces 50 with respect to the outer periphery of the main body 46 correspond to the respective dimensions of the jaws 48.

A cylindrical recess which departing from a face side 52 of the jaws 48 which is away from the main body 46 extends parallel to the longitudinal extension of the motor shaft 28 and the drive shaft 36 respectively, in the direction of the main body 46, is formed on each of the jaws 48 of the two coupling halves 42 and 44. A permanent magnet 54 is arranged in each of these recesses in each case, wherein a face side of the permanent magnets 54 which is away from the main body 46 is essentially aligned to the face side 52 of the jaw 48.

With regard to the permanent magnets 54, it is the case of rod magnets. These are inserted in each case into the recesses formed on the jaws 48 of the two coupling halves 42 and 44, such that the end of the permanent magnets 54 which is aligned to the face side 52 of the jaw 48 contains the north pole of the permanent magnets 54, whereas the other end of the permanent magnets 54 which is adjacent the base of the recess forms their south pole. However, here it is to be noted once again that the permanent magnets 54 could also be inserted into the recesses of the jaws 48 of the two coupling halves 42 and 44 in the reverse manner, so that the end of the permanent magnets 54 which is aligned to the face side 52 of the jaws 48 in each case contains their south pole. What is decisive however, is merely the fact that all permanent magnets 54 of both coupling halves 42 and 44 are arranged such that in each case the same pole points in the direction of the respective other coupling half 42 and 44 respectively.

Figure 7:
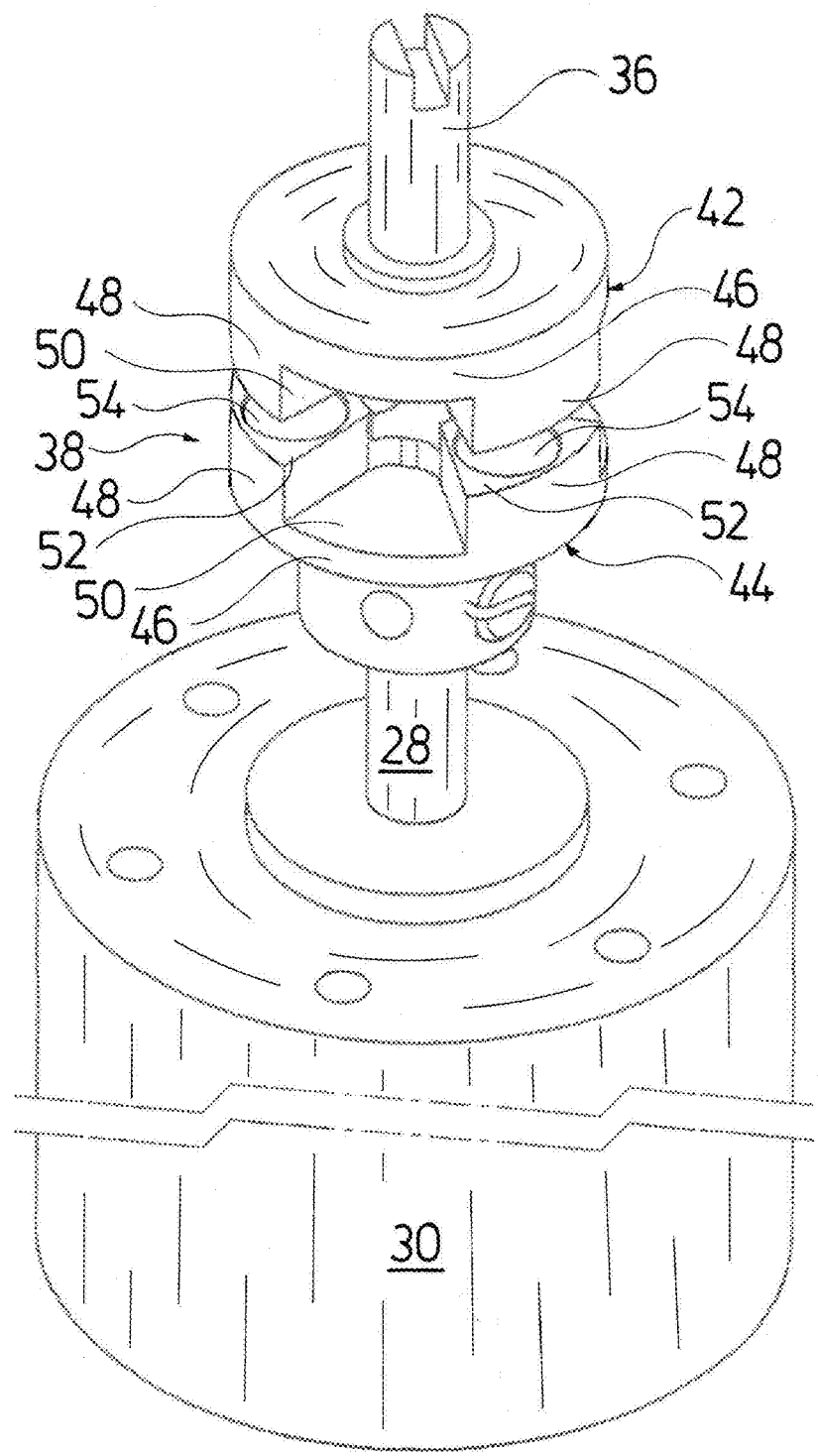
FIG. 7 is a perspective view of the motor and the coupling according to FIGS. 5 and 6, with the coupling in a first non-coupled condition.
Figure 8:
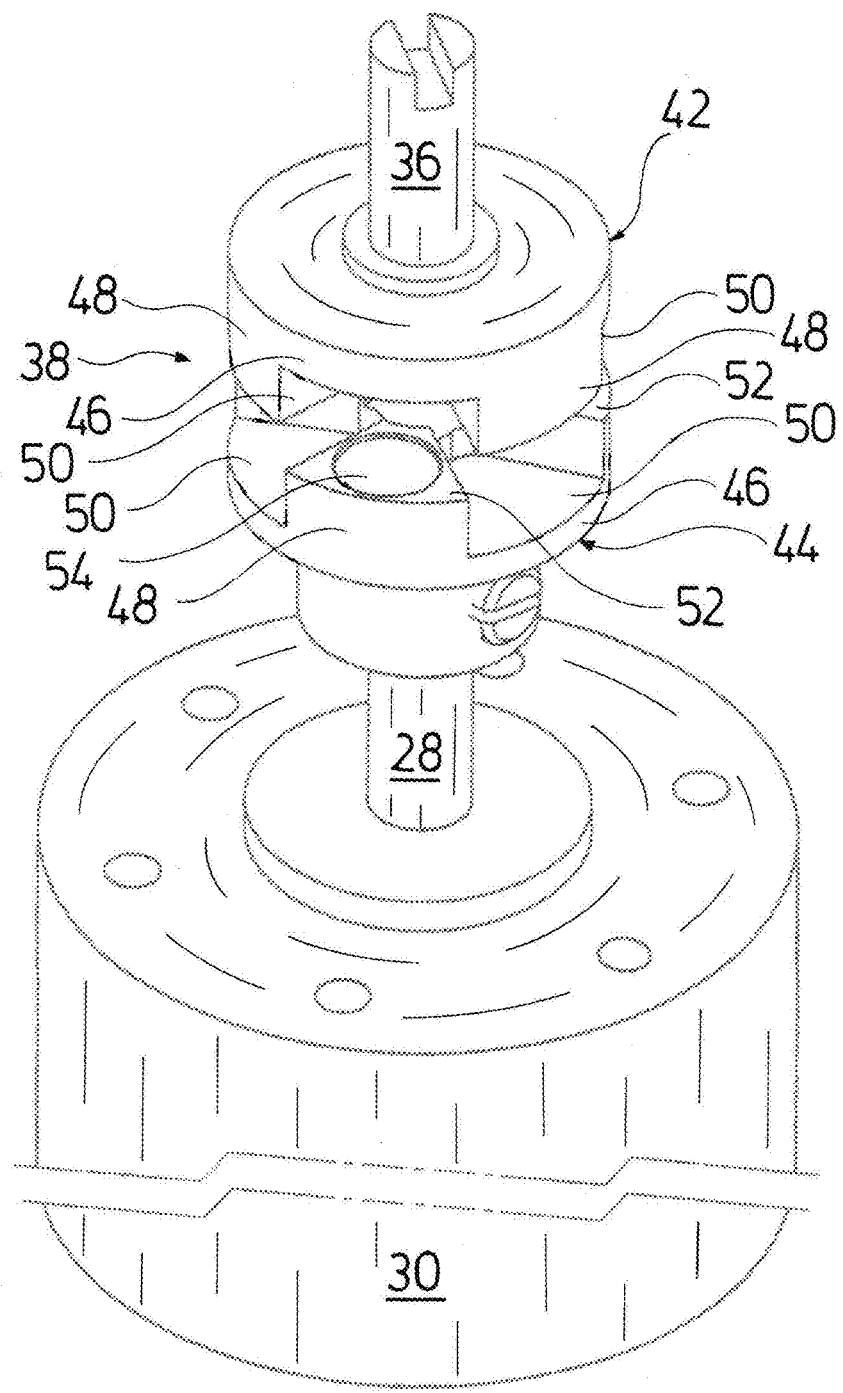
FIG. 8 is a perspective view of the representation according to FIGS. 5 and 6 with the coupling in a second, non-coupled condition.
Figure 9:
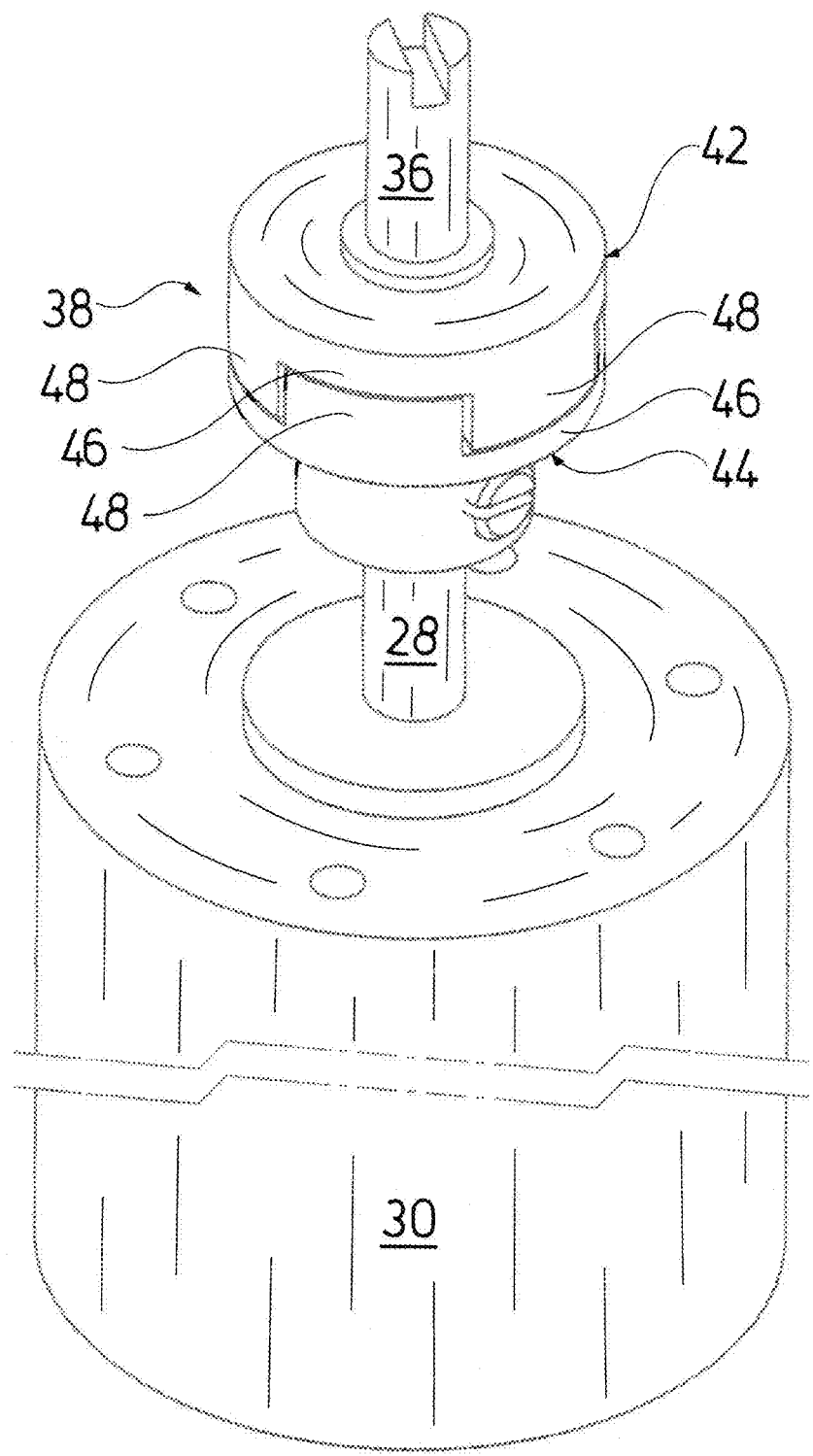
FIG. 9 is a perspective view of the representation according to FIGS. 5 and 6 with the coupling in the coupled condition (state)
Figure 10:
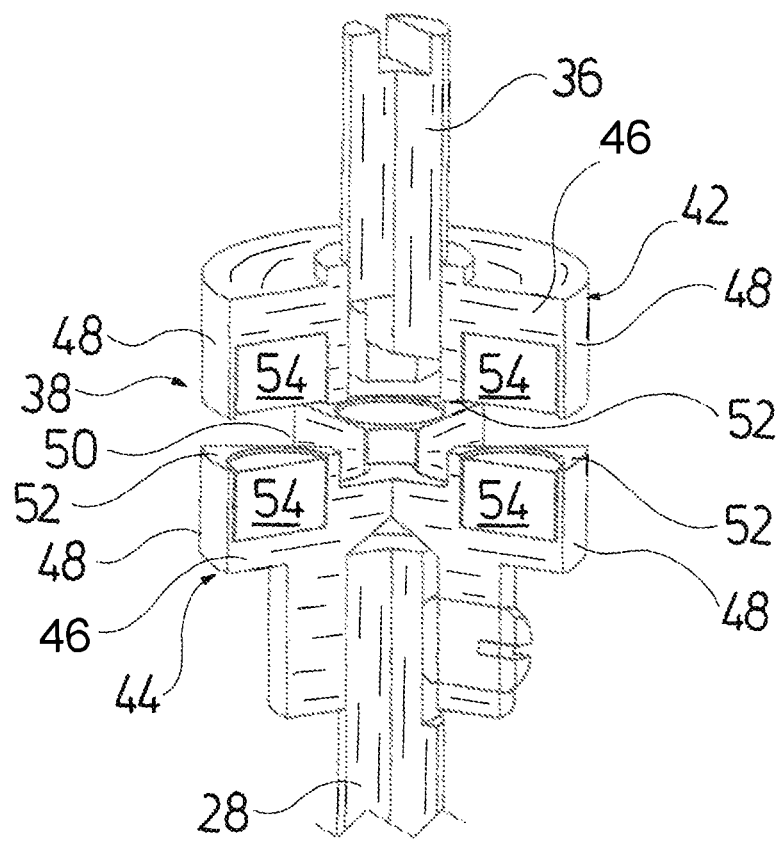
FIG. 10 is a sectional view of the coupling according to FIGS. 7-9 in the non-coupled condition.
Figure 11:
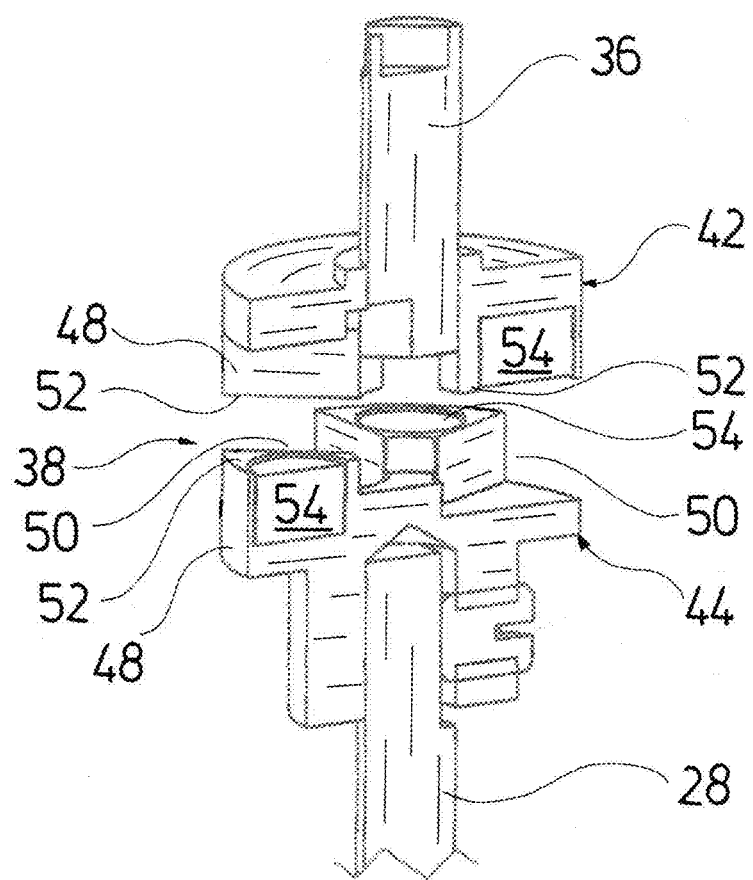
FIG. 11 is a sectional view of the coupling according to FIG. 10 in the coupled condition.

The significance of the permanent magnets 54 which are inserted in the jaws 48 of the coupling halves 42 and 44 and of their alignment is evident from FIGS. 7-11. The coupling half 44 which is arranged on the motor shaft 28, when attaching the motor 30 on the endoscope is connected to the coupling half 42 arranged on the drive shaft of the belt pulley 34 by way of an insert (plug-in) connection. Hereby, as is represented in FIGS. 7 and 10, it can be the case that the angular position of the coupling halves is not such that the jaws 48 of the coupling half 44 can engage into the intermediate spaces 50 between the jaws 48 of the coupling half 42, since the jaws 48 of the coupling half 44 completely or partly overlap the jaws 48 of the coupling half 42. In this case, magnetic repulsion forces which also include a force component in the rotation direction of the coupling halves 42 and 44 transverse to the approach direction of the coupling halves 42 and 44, arise between the permanent magnets 54 of the coupling halves 42 and 44 which are arranged in the jaws 48, when the coupling half 44 approaches the coupling half 42. The coupling halves 42 and 44 are rotated relative to one another by way of these force components, in a manner such that the jaws 48 of the coupling half 44 lie opposite the intermediate spaces 50 of the coupling half 42, as is represented in FIGS. 8 and 11. Then, as is evident from FIG. 9, the jaws 48 of the coupling half 44 engage into the intermediate spaces 50 of the coupling half 42 due to the further approach of the coupling half 44 onto the coupling half 42, by which means the coupling halves 42 and 44 are connected to one another with a positive fit.

While specific embodiments of the invention have been shown and described in detail to illustrate the application of the principles of the invention, it will be understood that the invention may be embodied otherwise without departing from such principles.

What is claimed is:

1. A releasable coupling for a transmission of a rotation movement, the releasable coupling comprising:
a first coupling half; and
a second coupling half, each of said first coupling half and said second coupling half comprising an engagement means, said engagement means corresponding to one another and said engagement means being positively engageable with one another, wherein at least one permanent magnet is arranged on at least one of said first coupling half and said second coupling half such that with an approach of said first coupling half and said second coupling half, said first coupling half and said second coupling half are rotated into a defined angular position relative to one another, with respect to a rotation axis, via a magnetic force produced by said permanent magnet, said first coupling half and said second coupling half forming a jaw coupling, said first coupling half comprising a first coupling half jaw, said second coupling half comprising a second coupling half jaw, said at least one permanent magnet being integrated in said first coupling half jaw and another permanent magnet being integrated in said second coupling half jaw, wherein an end of said at least one permanent magnet is flush with a planar axial face side of said first coupling half jaw and an end of said another permanent magnet is flush with a planar axial face side of said second coupling half jaw, said poles of said permanent magnets being aligned in a direction of said rotation axis of the coupling, wherein said permanent magnets of said first coupling half and said second coupling half arranged opposite one another face one another with a same pole.

2. A releasable coupling according to claim 1, wherein at least one permanent magnet is arranged on said first coupling half and at least one permanent magnet is arranged on said second coupling half to provide a plurality of permanent magnets, said permanent magnets being aligned, with respect to poles of said permanent magnets, such that said permanent magnets repel one another in a rotation direction of said first coupling half and said second coupling half.

3. A releasable coupling according to claim 2, wherein said at least one permanent magnet associated with said first coupling half is arranged on a front side of said first coupling half and said at least one permanent magnet associated with said second coupling half is arranged on a front side of said second coupling half, said front side of said first coupling half facing said front side of said second coupling half.

4. A releasable coupling according to claim 1, wherein at least one first coupling half projection and at least one first coupling half recess are formed on said first coupling half and at least one second coupling half projection and at least one second coupling half recess are formed on said second coupling half, said first coupling half projection engaging into said at least one second coupling half recess, said at least one second half projection engaging into said at least one first coupling half recess, wherein said at least one permanent magnet is integrated in said first coupling half projection and another permanent magnet is integrated in said second coupling half projection.

5. A releasable coupling according to claim 1, wherein said first coupling half and said second coupling half are formed from a non-magnetizable material.

6. A releasable coupling according to claim 1, wherein said first coupling half comprises a plurality of permanent magnets uniformly distributed over a periphery of said first coupling half, said second coupling half comprising a plurality of permanent magnets uniformly distributed over a periphery of said second coupling half.

7. A releasable coupling according to claim 6, wherein said plurality of permanent magnets associated with said first coupling half and said plurality of permanent magnets associated with said second coupling half are arranged at a same radial distance to said rotation axis of said coupling, said plurality of permanent magnets associated with said first coupling half being arranged on said first coupling half, said plurality of permanent magnets associated with said second coupling half being arranged on said second coupling half.

8. A releasable coupling according to claim 6, wherein said plurality of permanent magnets associated with said first coupling half and said plurality of permanent magnets associated with said second coupling half are arranged at a largest possible radial distance to said rotation axis of said coupling.

9. A releasable coupling according to claim 1, wherein said planar axial face side of said first coupling half jaw and said planar axial face side of said second coupling half jaw are perpendicular to a longitudinal axis of at least one of said first coupling half and said second coupling half.

10. An endoscopic instrument, comprising:
a tool arranged at a distal end of the instrument, said tool being actively connected to a motor via a coupling, wherein the coupling comprises a releasable coupling, said releasable coupling comprising a first coupling half and a second coupling half, each of said first coupling half and said second coupling half comprising an engagement means, said engagement means corresponding to one another and said engagement means being positively engageable with one another, wherein at least one permanent magnet is arranged on at least one of said first coupling half and said second coupling half such that with an approach of said first coupling half and said second coupling half, said first coupling half and said second coupling half are rotated into a defined angular position relative to one another, with respect to a rotation axis, via a magnetic force produced by said permanent magnet, said first coupling half and said second coupling half forming a jaw coupling, said first coupling half comprising a first coupling half jaw, said second coupling half comprising a second coupling half jaw, said at least one permanent magnet being integrated in said first coupling half jaw and another permanent magnet being integrated in said second coupling half jaw, wherein an end of said at least one permanent magnet is flush with a planar axial face side of said first coupling half jaw and an end of said another permanent magnet is flush with a planar axial face side of said second coupling half jaw, wherein poles of said at least one permanent magnet and said another permanent magnet being aligned in a direction of said rotation axis, wherein said at least one permanent magnet of said first coupling half and said another permanent magnet of said second coupling half arranged opposite one another face one another with a same pole.

11. An endoscopic instrument according to claim 10, wherein at least one permanent magnet and another permanent magnet provide a plurality of permanent magnets, said permanent magnets being aligned, with respect to poles of said permanent magnets, such that said permanent magnets repel one another in a rotation direction of said first coupling half and said second coupling half.

12. An endoscopic instrument according to claim 11, wherein said first coupling half and said second coupling half are formed from a non-magnetizable material.

13. An endoscopic instrument according to claim 11, wherein said planar axial face side of said first coupling half is located axially opposite a front side of said second coupling half with respect to a longitudinal axis of coupling.

14. An endoscopic instrument according to claim 10, wherein at least one first coupling half recess is formed on said first coupling half and at least one second coupling half recess is formed on said second coupling half, said first coupling half jaw defining at least a portion of said at least one first coupling half recess, said second coupling half jaw defining at least a portion of said at least one second coupling half recess, said first coupling half jaw engaging into said at least one second coupling half recess, said at least one second half jaw engaging into said at least one first coupling half recess, said planar axial face side of said first coupling half jaw and said planar axial face side of said second coupling half jaw being perpendicular to a longitudinal axis of at least one of said first coupling half and said second coupling half.

15. An endoscopic instrument according to claim 10, wherein said first coupling half comprises a plurality of permanent magnets uniformly distributed over a periphery of said first coupling half, said second coupling half comprising a plurality of permanent magnets uniformly distributed over a periphery of said second coupling half.

16. An endoscopic instrument according to claim 15, wherein said plurality of permanent magnets associated with said first coupling half and said plurality of permanent magnets associated with said second coupling half are arranged at a same radial distance to said rotation axis of said coupling, said plurality of permanent magnets associated with said first coupling half being arranged on said first coupling half, said plurality of permanent magnets associated with said second coupling half being arranged on said second coupling half.

17. An endoscopic instrument according to claim 15, wherein said plurality of permanent magnets associated with said first coupling half and said plurality of permanent magnets associated with said second coupling half are arranged at a largest possible radial distance to said rotation axis of said coupling.

18. A releasable coupling for a transmission of a rotation movement, the releasable coupling comprising:
a first coupling half; and
a second coupling half, each of said first coupling half and said second coupling half comprising an engagement structure, said engagement structure corresponding to one another and said engagement structure being positively engageable with one another, wherein at least one permanent magnet is arranged on at least one of said first coupling half and said second coupling half such that with an approach of said first coupling half and said second coupling half, said first coupling half and said second coupling half are rotated into a defined angular position relative to one another, with respect to a rotation axis, via a magnetic force produced by said permanent magnet, said engagement structure of said first coupling half comprising a first coupling half projection, said first coupling half projection comprising a first coupling half projection planar surface, said first coupling half projection planar surface being arranged axially opposite said second coupling half with respect to a longitudinal axis of said first coupling half, said engagement structure of said second coupling half comprising a second coupling half projection, said second coupling half projection comprising a second coupling half projection planar surface, said second coupling half projection planar surface being arranged axially opposite said first coupling half with respect to said longitudinal axis of said first coupling half, said at least one permanent magnet being integrated in said first coupling half projection and another permanent magnet being integrated in said second coupling half projection, said at least one permanent magnet comprising a first planar magnet surface, said first planar magnet surface being aligned with said first coupling half projection planar surface, said another permanent magnet comprising a second planar magnet surface, said second planar magnet surface being aligned with said second coupling half projection planar surface, wherein poles of said permanent magnet and said another permanent magnet are aligned in a direction of said rotation axis, wherein said permanent magnet of said first coupling half and said another permanent magnet of said second coupling half are arranged opposite one another and face one another with a same pole.

19. A releasable coupling according to claim 18, wherein said first coupling half projection planar surface, said first planar magnet surface, said second coupling half projection planar surface and said second planar magnet surface are perpendicular to said longitudinal axis.

\* \* \* \* \*